United States Patent [19]

Bowie et al.

[11] 4,056,384

[45] Nov. 1, 1977

[54] PESTICIDAL DIHYDROTETRAZOLO [1,5-a] QUINAZOLINES AND PESTICIDAL USES THEREOF

[75] Inventors: Raymond Alexander Bowie, Macclesfield; John Michael Cox; Gordon Michael Farrell, both of Wokingham; Margaret Claire Shephard, Maidenhead, all of England

[73] Assignee: Imperial Chemical Industries Limited, London, England

[21] Appl. No.: 607,543

[22] Filed: Aug. 25, 1975

[30] Foreign Application Priority Data

Sept. 5, 1974  United Kingdom .............. 38796/74

[51] Int. Cl.² .................... A01N 21/02; C07D 487/04
[52] U.S. Cl. ................................ 71/92; 260/256.4 F; 260/256.5 R
[58] Field of Search .................. 260/256.4 F, 256.5 R; 71/92

[56] References Cited

U.S. PATENT DOCUMENTS

| | | | |
|---|---|---|---|
| 3,835,137 | 9/1974 | Wagner | 260/256.4 F |
| 3,835,138 | 9/1974 | Wagner | 260/256.4 F |
| 3,838,126 | 9/1974 | Wagner | 260/256.4 F |
| 3,920,654 | 11/1975 | Edamura et al. | 260/256.4 F |

OTHER PUBLICATIONS

Vereshchagina, et al, "Chemical Abstracts", vol. 61 (1964), col. 8307(f).
"Chemical Abstracts", vol. 56, col. 7320c.
"Chemical Abstracts", vol. 54, col. 9939b.
"Chemical Abstracts", vol. 59, col. 13987a.
"Chemical Abstracts", vol. 60, col. 1743e.
"Chemical Abstracts", vol. 45, col. 4245e.
"Chemical Abstracts", vol. 27, col. 1632x.
"Chemical Abstracts", vol. 79, col. 92148m.
"Chemical Abstracts", vol. 47, col. 7507h.
"Chemical Abstracts", vol. 45, col. 5120.
"Chemical Abstracts", vol. 75, col. 63724.
"Chemical Abstracts", vol. 55, col. 2665e.
Greiss, "Berichte", vol. 13, pp. 977-979.

*Primary Examiner*—Donald G. Daus
*Assistant Examiner*—James H. Turnipseed
*Attorney, Agent, or Firm*—Cushman, Darby & Cushman

[57] ABSTRACT

Dihydrotetrazolo [1,5-a] quinazolines having the formula

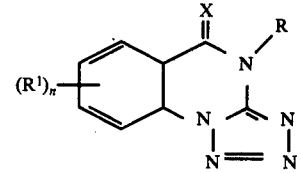

wherein (a) n is zero, X is oxygen, and R is optionally unsubstituted alkyl, alkenyl of at least 4 carbon atoms, alkynyl, aryl, aralkyl, alkylthio, cycloalkyl, amino or substituted aryl; or (b) n is 1 or 2, X is oxygen, R is hydrogen, or optionally-substituted alkyl, alkenyl, alkynyl, aryl, aralkyl, alkylthio, cycloalkyl, or amino, and $R^1$ is hydroxy, halogen, nitro, alkyl or alkoxy or (c) n is zero, 1 or 2, X is sulphur, R is hydrogen, or optionally-substituted alkyl, alkenyl, alkynyl, aryl, aralkyl, alkylthio, cycloalkyl, or amino, and $R^1$ is hydroxy, halogen, nitro, alkyl or alkoxy; or (d) n is 0, 1 or 2, X is $NR_2$ where $R_2$ is hydrogen, alkyl having 1 to 10 carbon atoms, benzyl or hydroxyalkyl, R is optionally-substituted alkyl, alkenyl, alkynyl, aryl, aralkyl, alkylthio, cycloalkyl, or amino, and $R^1$ is hydroxy, halogen, nitro, alkyl or alkoxy; and salts thereof. These compounds demonstrate pesticidal activity.

2 Claims, No Drawings

PESTICIDAL DIHYDROTETRAZOLO [1,5-a] QUINAZOLINES AND PESTICIDAL USES THEREOF

This invention relates to pesticidal dihydrotetrazolo [1,5-a] quinazolinones, thiones and imines. More particularly the invention relates to methods for combating pests, especially fungi; compositions therefor; and to certain novel dihydrotetrazolo [1,5-a] quinazolinones, thiones and imines and processes for preparing them.

The present invention provides novel dihydrotetrazolo [1,5-a] quinazoline derivatives having the formula:

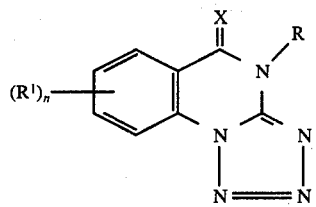

wherein R is hydrogen, or an optionally-substituted amino, alkyl, alkenyl, alkynyl, cycloalkyl, aralkyl, aryl, alkoxy, arylthio or alkylthio group; X is oxygen or sulphur or, when R is other than hydrogen, $NR^2$ where $R^2$ is hydrogen or an optionally-substituted alkyl, aryl, aralkyl, or amino group; n is zero or an integer of value 1 to 4 and $R^1$ is hydroxy, halogen, nitro, cyano or an optionally-substituted amino, alkyl, alkoxy, alkylthio, alkylsulphonyl, acyl, or aroyl group, or is carboxy- or sulphonic-acid, -ester or -amide; and salts thereof when R represents hydrogen or optionally substituted amino or when X is $NR^2$; provided that when n is zero and X is oxygen R is not hydrogen, allyl, phenyl or ortho-tolyl.

Whilst it is stated in this specification and claims that R can be alkenyl and alkynyl, that is it can represent, for example, the groups —CH$_2$—CH=CH$_2$ or —CH$_2$—C≡CH, it is not intended that the terms "alkenyl" and "alkynyl" include radicals or groups having a double or triple bond between the first and second carbon atoms counted away from the N-atom; Thus, for example, the radicals —C≡C—CH$_3$ and —CH=CH—CH$_3$ are excluded.

In the foregoing, and, where appropriate, in subsequent paragraphs, alkyl groups for R, $R^1$ and $R^2$ may be straight or branch chain and contain from 1 to 10 carbon atoms, but groups containing from 1 to 7 carbon atoms are preferred; for $R^2$ groups containing from 1 to 4 carbon atoms, and for R and $R^1$ groups containing from 1 to 2 carbon atoms respectively, are even further preferred. Examples of suitable alkyl groups are, for example, methyl, ethyl, propyl, butyl, amyl, hexyl, heptyl, allyl, and propynyl. Alkenyl and alkynyl groups are preferred which contain 3 or 4 carbon atoms.

Substituted amino, alkyl, aryl, aralkyl, alkoxy, arylthio, cycloalkyl, alkenyl, aklynyl, acyl, aroyl, and arylsulphonyl groups may bear as substituents, for example:- halogen atoms such as chlorine, bromine, fluorine and iodine; pseudo-halogen groups such as, for example, cyano, isocyano, thiocyanato, isothiocyanato, azido and the like; amino, hydroxy, mercapto, hydrocarbyl-thio, -sulphinyl or -sulphonyl groups, which may themselves bear a substituent group; carboxylic, or sulphur-containing, acid groups and esters and amides thereof; similar heterocyclic groups; nitro groups, carboxylic acyl groups; and groups containing aldehyde and/or ketonic functions.

In a preferred aspect the invention provides dihydrotetrazolo [1,5-a] quinazoline derivatives having the formula:

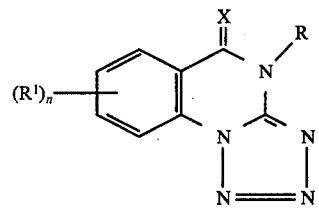

wherein n is zero, 1 or 2 and each $R^1$ is hydroxy, halogen, nitro, alkyl or alkoxy; X is oxygen or sulphur or, when R is other than hydrogen, $NR^2$ where $R^2$ is hydrogen, alkyl having 1 to 10 carbon atoms, benzyl or hydroxyalkyl; R is hydrogen, or an optionally-substituted alkyl, alkenyl, alkynyl, aryl, aralkyl, alkylthio, cycloalkyl, or amino group; and salts thereof when R is hydrogen or optionally substituted amino or when X is $NR^2$; provided that when n is zero and X is oxygen R is not hydrogen, allyl, phenyl, or ortho-tolyl.

In a more preferred aspect the invention provides dihydrotetrazolo [1,5-a] quinazoline derivatives having the formula:

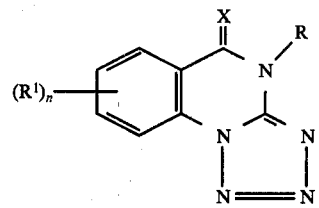

wherein R is hydrogen, allyl, amino, dimethylamino, trichloromethylthio, alkyl containing from 1 to 7 carbon atoms optionally-substituted with acetyl, benzoyl, thiocyanato, methylthio, chlorine or methoxy, phenyl optionally-substituted with chlorine; X is oxygen or sulphur, or, when R is other than hydrogen, $NR^2$ where $R^2$ is hydrogen, alkyl containing from 1 to 10 carbon atoms, benzyl or hydroxyalkyl; n is zero, one or two; $R^1$ is methyl, chloro, hydroxy or methoxy, at any one or more of the 7, 8 and 9 positions of the ring; and salts thereof when R is hydrogen or optionally substituted amino or when X is $NR^2$; provided that when n is zero and X is oxygen R is not hydrogen, allyl or phenyl.

The present invention, in an even more preferred aspect provides dihydrotetrazolo [1,5-a]quinazoline derivatives having the formula:-

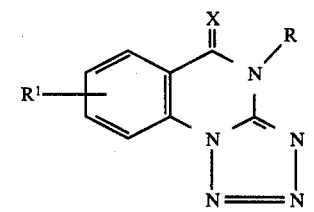

wherein X is oxygen or sulphur or, when R is other than hydrogen, $NR^2$ where $R^2$ is hydrogen, or alkyl or hydroxyalkyl containing from 1 to 4 carbon atoms; R is an alkyl radical containing from 1 to 2 carbon atoms or hydrogen; $R^1$ is hydrogen, methyl or methoxy at either the 7- or 9-ring position; and salts thereof; provided that when $R^1$ is hydrogen and X is oxygen R is not hydrogen.

In particular this invention provides the compounds having the structural formulae:-

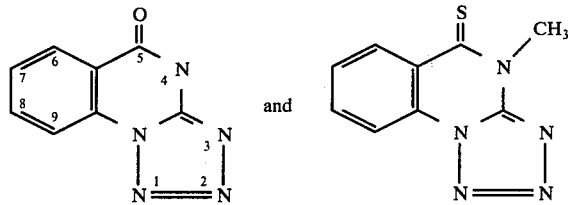

the ring numbering being as shown, and having the chemical names 4-methyl-4,5dihydro-tetrazolo [1,5-a] quinazolin-5-one and 4-methyl-4,5-dihydrotetrazolo [1,5-a] quinazolin-5-thione.

The compounds of the invention may be made, for example, by reacting a 2-mercapto or 2-alkylthio-3,4-dihydroquinazolin-4-one, optionally substituted at 3,5,6,7 and 8, with hydrazine hydrate and treating the product with nitrous acid. In certain cases (e.g. $R^1$ = OH), the reaction conditions are such that it is preferable to protect the substituent (e.g. as a carbonate) for some of the reaction sequences and to remove protection at some suitable later stage.

Alternatively an optionally substituted alkyl 2(5'-mercaptotetrazol-1'yl) benzoate may be treated successively with an N-monosubstituted-chloroacetamide, an oxidising agent, a base (e.g. 1,5-diazobicyclo [4.3.0] non-5-ene), sodium hydroxide and finally, if necessary, hydrochloric acid or thionyl chloride.

Alternatively an appropriately 6-,7-,8-, and 9-substituted 4,5-dihydrotetrazolo [1,5-a] quinazolin-5-one may be subjected to reaction under basic conditions with a compound having an electrophilic centre e.g. one having a labile halogen atom and, if desired, the product reacted further.

Substitution at one or more of the positions 6,7,8 and 9 may also be achieved by suitable treatement (s), e.g. ring nitration or hydroxyl methylation, of a compound already containing the tetrazole [1,5-a] quinazoline ring system.

5-Thiones may be made by treating the 5-ones with phosphorous pentasulphide preferably in the presence of either bromine or mercuric chloride. 5-Imino derivatives can be prepared from the thiones by reaction with an amine in the presence of mercuric chloride.

The compounds where R is a substituted amino function can be made, for example, by successive treatments of an optionally substituted alkyl isothiocyanatobenzoate with a hydrazine, a base (e.g. sodium hydride), hydrazine hydrate and nitrous acid whereas the unsubstituted (R = $NH_2$) examples arise from alkyl 2(5'-methanesulphonyltetrazol-1'-yl) benzoates by treatment with hydrazine.

In so far as these methods are new, or are applied to the preparation of the novel compounds defined herein, they form part of the present invention.

By the terms "pests," "pesticide," "pesticidal" used in this specification are intended pathogens harmful to plants, e.g. fungi, bacteria and viruses; and unwanted vegetation, e.g. algae.

The compounds, and compositions containing them, are variously active against the following diseases:

| Seed and Soil-Borne Fungal Diseases: | | |
|---|---|---|
| Disease (Latin Name) | Examples of Host Crop | Disease (Ordinary Name) |
| Pythium ultimum | Peas | Damping Off |
| Fusarium oxysporum | Tomato | Wilt |
| Septoria nodorum | Wheat | Glume Blotch |
| Rhizoctonia solani | Cotton | Sore Shin |
| Phytophthora cinnamomi | Avacado | Root rot |

| Foilage-borne Diseases: | | |
|---|---|---|
| Disease (Latin Name) | Examples of Host Crop | Disease (Ordinary Name) |
| Cochliobulus miyabeanus | Rice | Helminthosporium |
| Alternaria tenuis | Cotton | Leaf spot |
| Puccinia recondita | Wheat | Rust |
| Phytophthora infestans | Tomatoes | Late Blight |
| Colletotrichum lindemethianum | Beans | Anthracnose |
| Plasmopara viticola | Vines | Downy mildew |
| Botrytis cinerea | Tomatoes or Strawberries | Grey Mould |
| Erysiphe graminis | Barley | Powdery mildew |
| Podosphaera leucotricha | Apples | Powdery mildew |
| Piricularia oryzae | Rice | Blast |
| Colletotrichum coffeanum | Coffee | Berry disease |

| Post-Harvest Fungal Diseases: | | |
|---|---|---|
| Fungal Disease Organism (Latin Name) | Examples of Host Crop | Disease (Ordinary Name) |
| Pullularia pullulans | Wood | Fungal growth |
| Chaetomium globosum | Fibrous Cotton | Mould |
| Cladosporium sphaerospermum | Vegetable material | Fungal growth |
| Trichoderma viride | Corn | Seed rot |
| Penicillium digitatum | Citrus | Green Mould |
| Gloeosporium musarum | Bananas | Anthracnose |
| Geotrichum candidum | Oranges | Sour rot |
| Aspergillus niger | Onions | Black mould |

| Bacterial Diseases: | | |
|---|---|---|
| Bacterial Disease Organism (Latin Name) | Examples of Host Crop | Disease (Ordinary Name) |
| Xanthomonas malvacearum | Cotton | Blackarm |
| Xanthomonas oryzae | Rice | Blight |
| Pseudomonas syringae | Beans, Stone Fruit | Dieback |
| Xanthomonas vesicatoria | Peppers | Bacterial spot |
| Erwinia amylovora | Apple, Pear | Fireblight |
| Pseudomonas tomato | Tomato | Bacterial speck |
| Erwinia carotovora | Potato | Soft rot |

Algae
Scenedesmus

Virus Diseases
Cucumber Mosaic Virus
Potato Virus Y
Tomato Virus Y

In a further aspect, therefore, this invention provides a process for combating pests, especially fungi and bacteria, which comprises treating the pests; or treating plants, seeds, harvested fruits or vegetables, infested with, or liable to infestation with the pests; or the locus of any of the foregoing; with a dihydrotetrazolo [1,5-a] quinazoline derivative or a composition comprising such a derivative, as herein defined.

The present invention further provides, therefore, a process for combating pests, especially fungi and bacteria which comprises treating pests, crops, plants, seeds, or harvested produce, or the locus thereof, with a dihydrotetrazolo [1,5-a] quinazoline derivative, or composition containing such a derivative, having the formula:

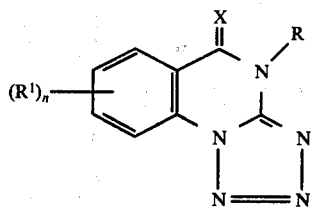

wherein R is hydrogen, or is an optionally substituted amino, alkyl, alkenyl, alkynyl, cycloalkyl, aralkyl, aryl, alkoxy, arylthio or alkylthio group; X is oxygen or sulphur, or when R is other than hydrogen, $NR^2$ where $R^2$ is hydrogen or an optionally substituted alkyl, aryl, aralkyl, or amino group; n is zero or an integer of value 1 to 4 and $R^1$ is hydroxy, halogen, nitro, cyano or an optionally substituted amino, alkyl, alkoxy, alkylthio, alkylsulphonyl, acyl, or aroyl group, or is carboxy- or sulphonic-acid, -ester or -amide; or a salt thereof when R represents hydrogen or optionally substituted amino or when X is $NR^2$.

In a preferred aspect the invention provides a process for combating pests which comprises treating pests, crops, plants or harvested produce, or the locus thereof, with a dihydrotetrazolo [1,5-a] quinazoline derivative, or composition containing such a derivative, having the formula:-

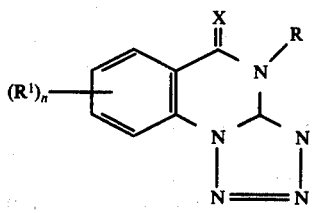

wherein n is zero, 1 or 2 and each $R^1$ is hydroxy, halogen, nitro, alkyl or alkoxy; X is oxygen or sulphur, or, when R is other than hydrogen, $NR^2$ where $R^2$ is hydrogen, alkyl having 1 to 10 carbon atoms, benzyl or hydroxyalkyl; R is hydrogen, or an optionally substituted alkyl, alkenyl, alkynyl, aryl, aralkyl, alkylthio, cycloalkyl, or amino group; or a salt thereof when R is hydrogen or optionally substituted amino or when X is $NR^2$.

In a more preferred aspect the invention provides a process for combating pests which comprises treating pests, crops, plants or harvested produce, or the locus thereof with a dihydrotetrazolo [1,5-a] quinazoline derivative, or a composition containing such a derivative, having the formula:

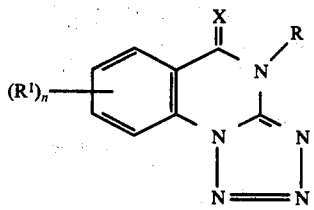

wherein R is hydrogen, allyl, amino, dimethylamino, trichloromethylthio, alkyl containing from 1 to 7 carbon atoms optionally substituted with acetyl, benzoyl, thiocyanato, methylthio, chlorine or methoxy; phenyl optionally-substituted with chlorine; X is oxygen or sulphur, or, when R is other than hydrogen, $NR^2$ where $R^2$ is hydrogen, alkyl containing from 1 to 10 carbon atoms, benzyl or hydroxyalkyl; n is zero, one or two; $R^1$ is a methyl, chloro, hydroxy or methoxy at any one or more of the 7, 8 and 9 positions of the ring; or a salt thereof when R is hydrogen or optionally substituted amino or when X is $NR^2$.

In a particularly preferred aspect the invention provides a process for combating pests which comprises treating pests, crops, plants or harvested produce, or the locus thereof, with a dihydrotetrazolo [1,5-a] quinazoline derivative, or a composition containing such a derivative, having the formula:-

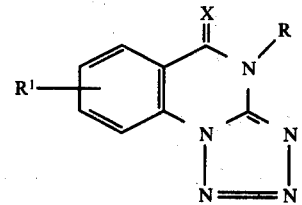

wherein X is oxygen or sulphur, or, when R is other than hydrogen, $NR^2$ where $R^2$ is hydrogen, or alkyl or hydroxyalkyl containing from 1 to 4 carbon atoms; R is an alkyl radical containing from 1 to 2 carbon atoms or hydrogen; $R^1$ is hydrogen, methyl or methoxy at either the 7- or 9- position of the ring; or a salf thereof.

In particular the invention provides a process for combating pests which comprises treating pests, crops, plants or harvested produce, or the locus thereof with a compound, or composition containing it, having the structural formula:-

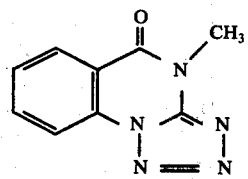

or the compound, or composition containing it, having the structural formula:-

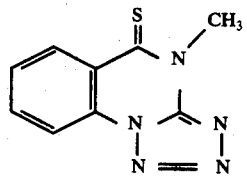

In a preferred, specific, process, the invention provides a process for combating the disease *Piricularia oryzae*, rice blast, which comprises applying to rice seeds, rice plants, the roots of rice plants, or to their locus, within or remote from, a germination or growing environment, a quinazoline derivative, or composition containing such a derivative, as defined herein.

In carrying the invention process into practical effect the growing crops, plants, seeds, or soil may be treated by any of the well-known and established procedures used in agriculture and crop protection. Thus, for example, the active compounds be applied as solids, liquids, solutions, dispersions, emulsions and these may comprise, in addition to the active substance, any other adjuvant useful for formulation purposes, or any other biologically active substance, for example to increase the number of diseases combated.

Such solid or liquid substances and formulations may be applied, for example, by any conventional technique, for example, by dusting, or otherwise applying the solid substances and formulations to the surfaces of growing crops, harvested produce, plants, seeds or soil, or to any part, or combination of parts thereof, or, for example, applying liquids or solutions for example, by dipping, spraying, mist blowing or soaking techniques.

The invention process is therefore useful for treating plants, seeds, harvested fruits, vegetables, or cut flowers infested with, or liable to infestation with any of the aforementioned specific fungal or bacterial diseases.

The term "seeds" is intended to include propagative plant forms generally and therefore includes, for example, cut stems, corms, tubers, rhizomes and the like.

The active compounds of this invention may be used alone to combat pests but are preferably formulated into compositions for this purpose. Preferred compositions contain, as an active ingredient, a preferred compound.

In a further aspect, therefore, the invention provides a pesticidal, especially fungicidal or bactericidal, composition comprising, as an active ingredient, a compound as defined in any of the preceding paragraphs; together with a carrier substance therefor. The carrier may be a solid or liquid diluent. In the case of a liquid diluent being used it is preferred that the composition then also contains a surface active (wetting) agent.

This invention is not, however, to be considered restricted to pesticidal compositions containing novel dihydrotetrazolo [1,5-a] quinazoline derivatives as defined herein and pesticidal compositions are within the scope of the invention which contain known dihydrotetrazolo [1,5-a] quinazoline derivatives.

The present invention further provides pesticidal compositions comprising, as an active ingredient, a dihydrotetrazolo [1,5-a] quinazoline derivative having the formula:

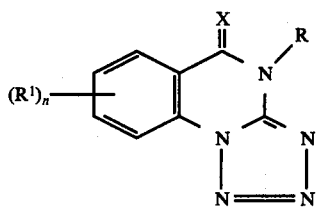

wherein R is hydrogen, or is an optionally-substituted amino, alkyl, alkenyl, alkynyl, cycloalkyl, aralkyl, aryl, alkoxy, arylthio or alkylthio group; X is oxygen or sulfur, or, when R is other than hydrogen, $NR^2$ where $R^2$ is hydrogen or an optionally-substituted alkyl, aryl, aralkyl, or amino group; n is zero or an integer of value 1 to 4 and $R^1$ is hydroxy, halogen, nitro, cyano or an optionally-substituted amino, alkyl, alkoxy, alkylthio, alkylsulphonyl, acyl, or aroyl group; or is carboxy-or sulphonic-acid, -ester or amide; or a salt thereof when R represents hydrogen or optionally-substituted amino or when X is $NR^2$.

In a more preferred aspect the invention provides pesticidal compositions comprising, as an active ingredient, a dihydrotetrazolo [1,5-a] quinazoline derivative having the formula:-

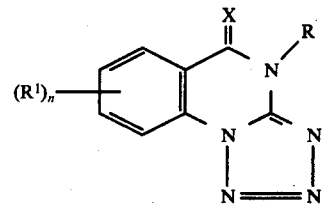

wherein n is zero, 1 or 2 and each $R^1$ is hydroxy, halogen, nitro, alkyl or alkoxy; X is oxygen or sulphur, or, when R is other than hydrogen, $NR^2$ where benzyl or hydroxyalkyl; R is hydrogen, or an optionally-substituted alkyl, alkenyl, alkynyl, aryl, aralkyl, alkylthio, cycloalkyl, or amino group; or a salt thereof when R is hydrogen or optionally substituted amino or when X is $NR^2$.

In an even more preferred aspect the invention provides pesticidal compositions comprising, as an active ingredient a dihydrotetrazolo [1,5-a] quinazoline derivative having the formula:

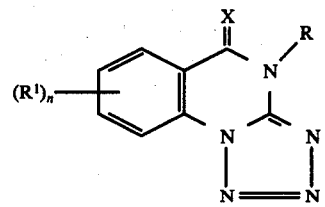

wherein R is hydrogen, allyl, amino, dimethylamino, trichloromethylthio, alkyl containing from 1 to 7 carbon atoms optionally substituted with acetyl, benzoyl, thiocyanato, methylthio, chlorine or methoxy; phenyl optionally substituted with chlorine; X is oxygen or sulphur, or, when R is other than hydrogen, $NR^2$ where $R^2$ is hydrogen, alkyl containing from 1 to 10 carbon atoms, benzyl or hydroxyalkyl; n is zero, one or two; R is methyl, chloro, hydroxy or methoxy at any one or more of the 7, 8 and 9 positions of the ring; or a salt thereof when R is hydrogen or optionally substituted amino or when X is $NR^2$.

In a particularly preferred aspect the invention provides a pesticidal composition comprising, as an active ingredient, a dihydrotetrazolo [1,5-a] quinazoline derivative having the formula:

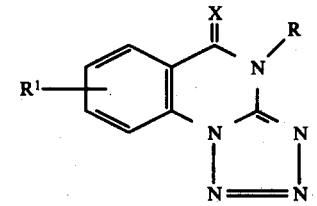

wherein X is oxygen or sulphur, or, when R is other than hydrogen, $NR^2$ where $R^2$ is hydrogen or alkyl or hydroxyalkyl containing from 1 to 4 carbon atoms; R is an alkyl radical containing from 1 to 2 carbon atoms or hydrogen; $R^1$ is hydrogen, methyl or methoxy at either the 7- or 9- position of the ring; or a salt thereof.

The invention, in particular, provides a pesticidal composition comprising, as an active ingredient, the compound having the structural formula:-

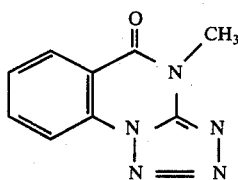

or the compound having the structural formula:

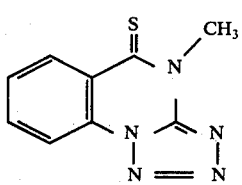

The compositions of the invention may be in the form of dusting powders or granules wherein the active ingredient is mixed with a solid diluent or carrier. Suitable diluents or carriers may be, for example, kaolin, bentonite, kieselguhr, dolomite, calcium carbonate, talc, powdered magnesia, Fuller's earth, gypsum, Hewitt's earth, diatomaceous earth and china clay. Compositions for dressing seed, for example, may comprise an agent assisting the adhesion of the composition to the seed, for example, a mineral oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The compositions may also be in the form of liquid preparations containing the active compound. Such liquid preparations for the invention process are generally solutions, aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example, sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonic acids. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol.

Other non-ionic agents are the partial esters derived from long chain fatty acids and hexitol anhydrides, the condensation products of the said partial esters with ethylene oxide, and the lecithins. Suitable suspending agents are, for example, hydrophilic colloids, for example, polyvinylpyrrolidone and sodium carboxymethylcellulose, and the vegetable gums, for example, gum acacia and gum tragacanth.

The aqueous solutions, dispersions or emulsions may be prepared by dissolving the active ingredient in an organic solvent which may contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example, for improving the distribution, adhesive power and resistance to rain on treated surfaces, the different compositions can be better adapted for the various uses for which they are intended.

The compositions may also be conveniently formulated by admixing them with fertilizers. A preferred composition of this type comprises granules of fertilizer material incorporating an invention compound. The fertilizer material may, for example, comprise nitrogen, or phosphate-containing substances.

The compositions which are to be used in the form of aqueous dispersions or emulsions are generally supplied in the form of a concentrate containing a high proportion of the active ingredient, the said concentrate to be diluted with water before use.

The concentrates are often required to withstand storage for prolonged periods and after such storage, to be capable of dilution with water in order to form aqueous preparations which remain homogeneous for a sufficient time to enable them to be applied by conventional spray equipment.

The concentrates may conveniently contain from 10–85% and generally from 10–60% by weight of the active ingredient. When diluted to form aqueous preparations, such preparations may contain varying amounts of the active ingredient depending upon the purpose for which they are to be used, but an aqueous preparation containing between 0.001% and 10% by weight of active ingredient may be used.

It is understood that the compositions of this invention may comprise, in addition to one or more active compounds according to the invention, one or more other substances having biological activity, for example, insecticidal, fungicidal, plant growth regulating, bactericidal or herbicidal activity.

This invention is illustrated, but not limited by, the following Examples, in which melting points, boiling points, and other temperatures, are expressed in degrees Centigrade.

EXAMPLE 1

This example illustrates the preparation of 4,5-dihydrotetrazolo [1,5-a] quinazolin-5-one having the structural formula:-

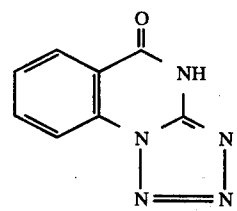

(Compound No. 1)

A mixture of 2-mercapto-3,4-dihydroquinazolin-4-one (18 g; prepared as described in J. Org. Chem., 1962, 27, 3701), hydrazine hydrate (100 ml) and ethanol (100 ml) was refluxed for 30 minutes. It was then cooled and the precipitate filtered off, washed with water and dried to give the 2-hydrazinoquinazolinone (7.6 g; m.p. > 300°). A stirred solution of this product (3.5 g) in hydrochloric acid (20 ml, 2N) and acetic acid (10 ml) was treated dropwise at 0°-5° with a solution of sodium nitrite (1.5 g) in water (10 ml). The mixture was allowed to warm to room temperature, filtered and dried to give the title compound (3.82 g, m.p. 237°-242°). Recrystallisation from ethanol gave material, m.p. 243°.

EXAMPLE 2

This example illustrates the preparation of 4-methyl-4,5-dihydrotetrazolo [1,5-a] quinazolin-5-one having the structural formula:-

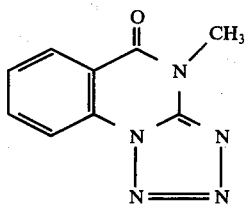

(Compound No. 2)

A mixture of anthranilic acid (22.5 g), methyl isothiocyanate (12.5 g) and ethanol (200 ml) was refluxed for three hours, cooled and the precipitate filtered off and washed with water. Recrystallisation from ethanol gave 2-mercapto-3-methyl-3,4-dihydroquinazolin-4-one (13.0 g, m.p. 265°-266°). A mixture of this material (5.76 g) hydrazine hydrate (20 ml) and ethanol (30 ml) was refluxed for 30 minutes, then cooled. The precipitate was filtered off, washed with water and dried to give the 2-hydrazinoquinazolinone (3.16 g, m.p. 220°-223°). Recrystallisation from ethanol gave material m.p. 223°. A stirred solution of the crude product (1.9 g) in a mixture of hydrochloric acid (20 ml, 2N) and acetic acid (10 ml) was treated dropwise at 0°-5° with a solution of sodium nitrite (0.69 g) in water (5 ml). The mixture was allowed to attain room temperature and, after one hour, was filtered and the precipitate washed with water and dried to give the title compound (1.04 g., m.p. 164°-167°). Recrystallisation from ethanol gave material m.p. 167°.

EXAMPLE 3

This example illustrates the preparation of 4-methyl-4,5-dihydrotetrazolo [1,5-a] quinazolin-5-one, by an alternative procedure to that described in Example 2.

A solution of 4,5-dihydrotetrazolo [1,5-a] quinazolin 5-one (1.8 g., prepared as described in Example 1) in dry N,N-dimethylformamide (20 ml) was added slowly to a suspension of sodium hydride (0.5 g, 50% suspension in mineral oil, prewashed with light petroleum) in dimethylformamide (10 ml). After 10 minutes methyl iodide (5 ml) was added and the mixture allowed to stand for 3 hours. It was then diluted with water and the precipitate washed with water and dried to give the title compound (1.9 g, m.p. 164°-166°). Recrystallisation from ethanol gave material m.p. 167°.

EXAMPLE 4

This example illustrates the preparation of 4-methyl-4,5-dihydrotetrazolo [1,5-a] quinazolin-5-one by an alternative procedure to those described in Examples 2 and 3.

A mixture of methyl 2-isothiocyanatobenzoate (19.0 g, prepared as described in J. Org. Chem., 1962, 27, 3701), sodium azide (9.85 g) and water (200 ml) was refluxed, with stirring, for thirty minutes. It was then cooled, filtered through kieselguhr and acidified with dilute hydrochloric acid to give methyl 2(5'-mercaptotetrazol-1'-yl) benzoate (17.28 g. m.p. 147°-8°).

A mixture of this material (11.35 g), sodium hydride (2.12 g, 50% dispersion in mineral oil, pre-washed with petroleum) and dry N,N-dimethylformamide (44 ml) was treated, with stirring at 0°, with N-methylchloroacetamide (5.24 g). It was stirred for eighteen hours, poured into ice-water and the precipitate filtered off and dried. Recrystallisation from methanol gave methyl 2[5'-(N-methylacetamidomethylthio) tetrazol-1'-yl] benzoate (8.52 g, m.p. 97°-8°).

A mixture of this material (7.0 g), acetic acid (58 ml), 2N sulphuric acid (58 ml) and potassium permanganate (5.8 g) was stirred at 5° for one hour, then decolorised by the addition of sodium metabisulphite. Water was added and the precipitate filtered off and washed with water. Recrystallisation from methanol gave methyl 2[5'-(N-methylacetamidomethanesulphonyl)tetrazol-1'-yl]benzoate (4.66 g, m.p. 138°-9°, decomp.).

A mixture of this material (3.4 g), 1,5-diazabicyclo[4.3.0]non-5-ene (1.2 g) and acetonitrile (28 ml) was refluxed for thirty minutes, cooled, diluted with water, acidified with dilute hydrochloric acid and extracted with chloroform. The extract was washed, dried and evaporated and the residue triturated with ether/petroleum and recrystallised from toluene to give methyl 2[5'-(N-acetylmethylamino)tetrazol-1'-yl]benzoate (2.45 g, m.p. 134°).

A solution of this compound (275 mg) in hot methanol (3 ml) was rapidly cooled and treated, at 5°, with N sodium hydroxide solution (6 ml). After stirring for five minutes, the mixture was filtered and the filtrate extracted with chloroform. The aqueous layer was acidified with dilute hydrochloric acid to give 2(5'-methylaminotetrazol-1'-yl) benzoid acid (90 mg, m.p. 152-4°).

A mixture of this compound (90 mg), ethanol (2 ml) and N hydrochloric acid (0.1 ml) was refluxed for twenty minutes and cooled to give the title compound (60 mg, m.p. 166°). It should be noted that this stage can also be catalysed by bases e.g. sodium hydroxide.

EXAMPLE 5

This example illustrates the preparation of 4-phenyl-4,5-dihydrotetrazolo [1,5-a] quinazolin-5-one having the structural formula:-

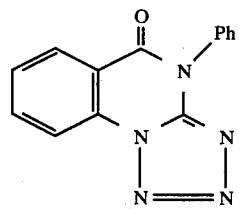

(Compound No. 3)

The sequence described in Example 2 was repeated using phenyl isothiocyanate (22 g) in place of methyl isothiocyanate. Further treatments with hydrazine hydrate in ethanol, then nitrous acid as described in Example 2 and in Chem. Abstracts 1964, 61, 8308a gave the title compound m.p. 190°.

EXAMPLE 6

This example illustrates the preparation of several 4-substituted 4,5-dihydrotetrazolo [1,5-a] quinazolin-5-ones having the structural formulae:-

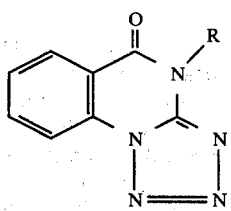

Methyl 2(5'-mercaptotetrazol-1'-yl)benzoate (prepared as described in Example 4) was subjected to successive reactions with an appropriately substituted N-aryl or N-alkyl-chloroacetamide (RNHCOCH$_2$Cl), an oxidising agent (e.g. potassium permanganate or hydrogen peroxide/trifluoroacetic acid) and 1,5-diazabicyclo [4.3.0] non-5-ene basically as described in Example 4. Whilst in some cases tricyclic products are formed directly, certain highly hindered examples [e.g. R = C(CH$_3$)$_3$, cyclohexyl ] yielded only the corresponding methyl 2[5'-(N-acetylalkylamino)tetrazol-1'-yl]benzoates. In these circumstances the ester and amide functions were cleaved by basic hydrolysis and the resulting products cyclized to the title compounds by refluxing in thionyl chloride.

TABLE 1

| COMPOUND NO | R | M.P. ° C |
|---|---|---|
| 4 | C(CH$_3$)$_3$ | 165-7 |
| 5 | cyclohexyl | 176-7 |
| 6 | 4-Cl—C$_6$H$_4$ | 283-4 |
| 7 | 2,4,5-Cl$_3$—C$_6$H$_2$ | 59-60 |
| 8 | 4-CH$_3$—C$_6$H$_4$ | 237 |

EXAMPLE 7

This example illustrates the preparation of a number of 4-substituted-4,5-dihydrotetrazolo [1,5-a] quinazolin-5-ones having the general structural formula:

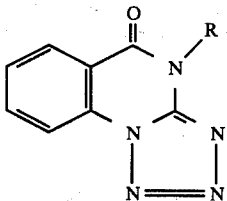

A solution of 4,5-dihydrotetrazolo [1,5-a] quinazolin-5-one (prepared as described in Example 1) in dry N,N-dimethylformamide was treated successively with sodium hydride (1 equivalent) in dimethylformamide and an appropriate alkyl halide (one or more equivalents) as described for the methyl derivative in Example 3. The reaction was allowed to proceed until complete, as indicated by thin layer chromatography, then terminated by addition of water. The product was then either filtered off or extracted with dichloromethane as appropriate. Substituents, melting points and yields are given in Table 2.

TABLE 2

| COMPOUND NO | R | M.P. ° C | YIELD % |
|---|---|---|---|
| 9 | C$_2$H$_5$ | 125 | 48 |
| 10 | (CH$_2$)$_2$CH$_3$ | 107 | 58 |
| 11 | CH(CH$_3$)$_2$ | 188 | 29 |
| 12 | (CH$_2$)$_3$CH$_3$ | 85 | 78 |
| 13 | (CH$_2$)$_4$CH$_3$ | 92 | 20 |
| 14 | (CH$_2$)$_5$CH$_3$ | 78 | 50 |
| 15 | (CH$_2$)$_6$CH$_3$ | 65 | 14 |
| 16 | (CH$_2$)$_7$CH$_3$ | 59 | 40 |
| 17 | CH$_2$Ph | 198 | 59 |
| 18 | CH$_2$CH=CH$_2$ | 133 | 55 |
| 19 | CH$_2$COCH$_3$ | 181 | 52 |
| 20 | CH$_2$COPh | 198 | 34 |
| 21 | CH$_2$CO$_2$CH$_3$ | 130 | 50 |
| 22 | (CH$_2$)$_2$CO$_2$C$_2$H$_5$ | 114 | 18 |
| 23 | CH$_2$CN | 200 | 53 |
| 24 | CH$_2$SCN | 182 | 69 |
| 25 | CH$_2$SCH$_3$ | 154 | 50 |
| 26 | CH$_2$C≡CH | 214 | 71 |

N.B. "Ph" signifies phenyl, i.e. C$_6$H$_5$. Thus CH$_2$Ph is benzyl.

EXAMPLE 8

This example illustrates the preparation of 5-oxo-4,5-dihydrotetrazolo [1,5-a] quinazolin-4-yl-acetic acid having the structural formula:

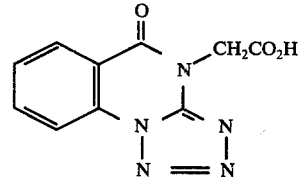

(Compound No. 27)

A mixture of methyl 5-oxo-4,5-dihydrotetrazolo [1,5-a] quinazolin-4-yl-acetate (3.8 g), concentrated hydrochloric acid (76 ml) and water (76 ml) was refluxed, with stirring, for one hour. It was then cooled and the solid filtered off, dried and recystallised from acetonitrile to give the title compound (1.82 g. m.p. 213°-6°, decomp.).

EXAMPLE 9

This example illustrates the preparation of 4-hydroxymethyl-4,5-dihydrotetrazolo [1,5-a] quinazolin-5-one having the structural formula:

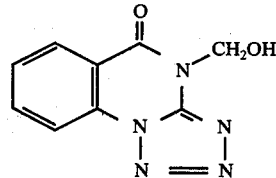

(Compound No. 28)

A mixture of 4,5-dihydrotetrazolo [1,5-a] quinazolin-5-one (4.0 g, prepared as described in Example 1), formaldehyde solution (20 ml, 40%) and water (40 ml) was heated on a steam bath for one hour. It was then cooled and the precipitate filtered off and washed successively with water, ethanol and ester to give the title compound (2.92 g. m.p. 245°).

EXAMPLE 10

This example illustrates the preparation of 4-chloromethyl-4,5-dihydrotetrazolo [1,5-a] quinazolin-5-one having the structural formula:

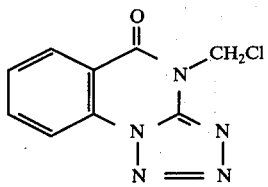

(Compound No. 29)

A mixture of 4-hydroxymethyl-4,5-dihydrotetrazolo [1,5-a] quinazolin-5-one (2.8 g, prepared as described in Example 9) and thionyl chloride (66 ml) was refluxed for thirty minutes, the excess reagent removed in vacuo and the residue triturated with petroleum. Recrystallisation from acetonitrile gave the title compound (1.88 g, m.p. 215°).

EXAMPLE 11

This example illustrates the preparation of 4-methoxymethyl-4,5-dihydrotetrazolo [1,5-a] quinazolin-5-one having the structural formula:

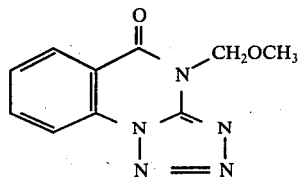

(Compound No. 30)

A mixture of 4-chloromethyl-4,5-dihydrotetrazolo [1,5-a] quinazolin-5-one (3.93 g, prepared as described in Example 10), sodium methoxide (prepared from 0.43 g sodium) and methanol (70 ml) was refluxed for three hours, cooled and diluted with water. The solid obtained was dried and recrystallized from ethanol to give the title compound (2.74 g, m.p. 156–8°).

EXAMPLE 12

This example illustrates the preparation of N-(5-oxo-4,5-dihydrotetrazolo[1,5-a] quinazolin-4-yl) methylpyridinium chloride having the structural formula:

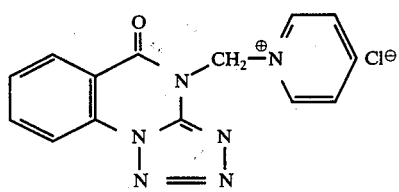

(Compound No. 31)

A mixture of 4-chloromethyl-4,5-dihydrotetrazolo [1,5-a] quinazolin-5-one (2.0 g, prepared as described in Example 10) and pyridine (60 ml) was refluxed for one hour, cooled and filtered. The solid was washed with ether and recrystallised from water to give the title compound (2.20 g, m.p. 263–4°).

EXAMPLE 13

This example illustrates the preparation of the sodium salt of 4,5-dihydrotetrazolo [1,5-a] quinazolin-5-one having the structural formula:

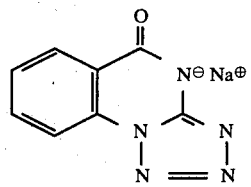

(Compound No. 32)

A mixture of 4,5-dihydrotetrazolo [1,5-a] quinazolin-5-one (6.16 g, prepared as described in Example 1), aqueous sodium hydroxide solution (33 ml 1N) and water (10 ml) was heated to 100° to give a clear solution, then evaporated to dryness. The residue was washed with acetone and a little methanol to give the sodium salt (5.93 g, m.p. > 300°) of the starting material. (Dissolution in water and acidification causes regeneration of the free acid).

EXAMPLE 14

This example illustrates the preparation of 4-trichloromethylthio-4,5-dihydrotetrazolo [1,5-a] quinazolin-5-one having the structural formula:

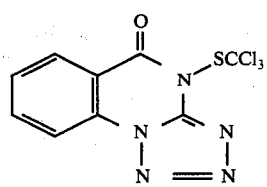

(Compound No. 33)

The sodium salt (2.1 g, prepared as described in Example 13) of 4,5-dihydrotetrazolo [1,5-a] quinazolin-5-one was finely ground, suspended in benzene (25 ml) and treated with trichloromethylsulphenyl chloride (1.15 ml). The mixture was stirred for 20 hours, diluted with water and extracted with chloroform. The extracts were washed, dried and evaporated to give a solid (2.5 g) which was recrystallized from acetonitrile to give the title compound (1.35 g, m.p. 192°–196°, decomp.).

EXAMPLE 15

This example illustrates the preparation of 4-dimethylamino-4,5-dihydrotetrazolo [1,5-a] quinazolin-5-one having the structural formula:

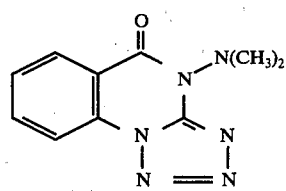

(Compound No. 34)

A solution of methyl 2-isothiocyanatobenzoate (6.0 g, prepared as described in J. Org. Chem., 1962, 27, 3701) and N,N-dimethylhydrazine (6 ml) in ethanol (60 ml) was stirred at room temperature for 1 hour. The precipitate was filtered off and dried to give methyl 2(3'-dimethylaminothioureido)benzoate (6.73 g, m.p. 149°–152°).

This material (8.0 g) was added cautiously to a stirred suspension of sodium hydride (2.0 g, 50% dispersion, prewashed with petroleum) in dry N,N-dimethylformamide (100 ml). The mixture was stirred for twenty hours, diluted with water, filtered through kieselguhr and neutralised with hydrochloric acid to give a precipitate of 3-dimethylamino-2-mercapto-3,4-dihydroquinazolin-4-one (6.43 g, m.p. 245–9°, after drying).

A mixture of this material (5.1 g), hydrazine hydrate (15.8 ml) and ethanol (23 ml) was refluxed for thirty minutes, diluted with water and cooled to give 3-dimethylamino-2-hydrazino-3,4-dihydroquinazolin-4-one (3.67 g, m.p. 125–7°, after drying).

A solution of sodium nitrite (0.48 g) in water (3 ml) was added dropwise, at 0°, to a stirred mixture of this hydrazine (1.5 g), 2N hydrochloric acid (14 ml) and acetic acid (7 ml). It was then stirred for a further one hour at room temperature and the precipitate filtered off, washed with water, and dried to give the title compound (1.4 g, m.p. 184°, decomp.).

EXAMPLE 16

This example illustrates the preparation of 4-amino-4,5-dihydrotetrazolo [1,5-a] quinazolin-5-one having the structural formula:

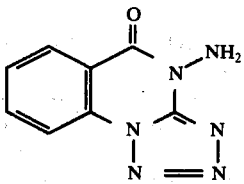

(Compound No. 35)

A suspension of methyl 2(5′-mercaptotetrazol-1′-yl) benzoate (4.30 g, prepared as described in Example 4) in N,N-dimethylformamide (60 ml) was treated successively with sodium hydride (1.0 g, 50% suspension, prewashed with petroleum) and methyl iodide (2 ml). The mixture was stirred overnight at room temperature, diluted with water, and the precipitate filtered off. Recrystallization from ethanol gave methyl (5′-methylthiotetrazol-1′-yl) benzoate (3.5 g, m.p. 132–4°, decomp.).

A mixture of this material (9.7 g), potassium permanganate (9.7 g), 2N sulphuric acid (100 ml) and acetic acid (100 ml) was stirred for 1 hour, then decolorized with sodium metabisulphite and diluted with water. The precipitate was dried and recrystallised from isopropanol to give methyl 2(5′-methanesulphonyltetrazol-1′-yl)benzoate (8.54 g, m.p. 130–4°).

A mixture of this material (2.0 g), hydrazine hydrate (3 ml) and ethanol (30 ml) was refluxed for ninety minutes, cooled and diluted with water. The precipitate was filtered off, washed with water and ethanol to give the title compound (0.96 g, m.p. 226°, decomp.).

EXAMPLE 17

This example illustrates the preparation of a number of 4,Ar-polysubstituted-4,5-dihydrotetrazolo [1,5-a] quinazolin-5-ones having the structural formulae:

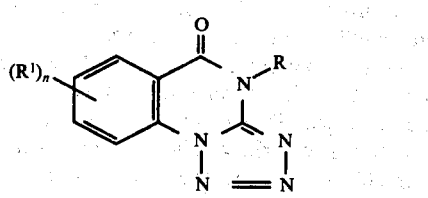

Appropriately substituted anthranilic acids were treated successively with an isothiocyanate, hydrazine hydrate and nitrous acid in a manner similar to that described in Examples 2 and 5. The products are exemplified in Table 3.

TABLE 3

| COMPOUND NO | R¹ | R | M.P. °C |
|---|---|---|---|
| 36 | 7-CH$_3$ | CH$_3$ | 168 |
| 37 | 7-CH$_3$ | C$_6$H$_5$ | 223 |
| 38 | 7-Cl | CH$_3$ | 222 |
| 39 | 9-CH$_3$ | CH$_3$ | 190 |
| 40 | 9-OCH$_3$ | CH$_3$ | 204 |
| 41 | 7-Cl, 8-OCH$_3$ | CH$_3$ | 266 |

EXAMPLE 18

This example illustrates the preparation of 7-hydroxy-4-methyl-4,5-dihydrotetrazolo [1,5-a] quinazolin-5-one having the structural formula:

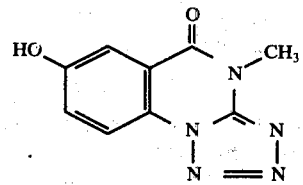

(Compound No. 42)

A stirred mixture of 3-formyl-4-nitrophenyl ethyl carbonate (33.1 g, prepared as described in J. Chem. Soc., 1925, 1195), potassium permanganate (17.0 g), acetic acid (33 ml) and acetone (330 ml) was cooled to keep the temperature below 50°, then allowed to stand at room temperature for a further forty-five minutes. Dilute sulphuric acid and chloroform were added and the mixture decolorised with sodium metabisulphite. The organic layer was extracted with sodium bicarbonate solution and the extracts acidified with dilute hydrochloric acid to give 3-carboxy-4-nitrophenyl ethyl carbonate (23.2 g, m.p. 132–7°).

A mixture of this material (4.0 g), dichloromethane (100 ml), water (100 ml) and sodium dithionite (20 g) was shaken vigorously for ten minutes and the organic phase washed, dried and evaporated to give 3-carboxy-4-aminophenyl ethyl carbonate (1.35 g, m.p. 157–8°).

A mixture of this material (5.2 g), methyl isothiocyanate (1.8 g) and ethanol (45 ml) was refluxed for four hours, cooled and filtered. The solid was washed with ethanol and ether to give 2-mercapto-3-methyl-4-oxo-3,4-dihydroquinazolin-6-yl ethyl carbonate (2.44 g, m.p. 216°–220°). This was treated with hydrazine hydrate (9 ml) in ethanol (18 ml) and refluxed for thirty minutes, cooled in ice and diluted with water. The precipitate was washed with water, ethanol and ether to give 2-hydrazino-6-hydroxy-3-methyl-3,4-dihydroquinazolin-4-one (1.23 g, m.p. > 300°). This was warmed with a mixture of 2N hydrochloric acid (10 ml) and acetic acid (5 ml), cooled to 0°, and diluted with dimethylsulphoxide (5 ml). A solution of sodium nitrite (0.43 g) in water (2 ml) was added dropwise at 0°, to the vigorously stirred mixture. After a further 1 hour at room temperature, the solid was filtered off, dried and recrystallised from ethanol to give the title compound (0.59 g, m.p. 279°–281°).

EXAMPLE 19

This example illustrates the preparation of 7-methoxy-4-methyl-4,5-dihydrotetrazolo [1,5-a] quinazolin-5-one having the structural formula:

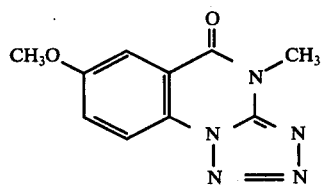

(Compound No. 43)

A mixture of 7-hydroxy-4-methyl-4,5-dihydrotetrazolo [1,5-a] quinazolin-5-one (108 mg), N sodium hydroxide solution (0.75 ml) and dimethylsulphate (0.095 ml) was stirred at 40°–50° for thirty minutes, additional base being added as necessary to maintain alkalinity. It was then cooled and the precipitate washed with water, dried and recrystallised from acetonitrile to give the title compound (25 mg, m.p. 183°).

EXAMPLE 20

This example illustrates the preparation of 7-(or 8-)-nitro-4-methyl-4,5-dihydrotetrazolo [1,5-a] quinazolin-5-one having the structural formula:

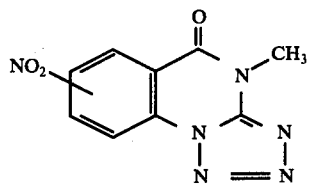

(Compound No. 44)

A mixture of 4-methyl-4,5-dihydrotetrazolo [1,5-a] quinazolin-5-one (4.0 g, prepared as described in Example 2), chloroform (20 ml) and concentrated sulphuric acid (15 ml) was cooled to 10° and treated with fuming nitric acid (1.1 ml). It was stirred overnight at room temperature, the layers separated and the acid layer added to ice-water. The precipitate was washed with water, dried and recrystallized from acetonitrile to give the title compound (3.8 g, m.p. 202–4°). Whether nitration occurred at the 7- or 8- position has not been established.

EXAMPLE 21

This example illustrates the preparation of 8-chloro-4-methyl-4,5-dihydrotetrazolo [1,5-a] quinazolin-5-one having the structural formula:

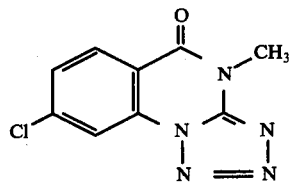

(Compound No. 45)

4-Chloroanthranilic acid (40 g) was converted, by treatment with hydrogen chloride in methanol, into its methyl ester (27.0 g, m.p. 62–4°). Successive reactions with thiophosgene, sodium azide, N-methyl-chloroacetamide and potassium permanganate, basically as described in Example 4 gave methyl 4-chloro-2[5'-(N-methylacetamidomethanesulphonyl) tetrazol-1'-yl]benzoate (m.p. 152–4°). Treatment with 1,5-diazabicyclo[4.3.0]non-5-ene in acetonitrile, as described in that Example gave an oily amide-ester which was instantaneously cyclized to the title compound (m.p. 235–7°) by treatment with sodium hydroxide solution.

EXAMPLE 22

This example illustrates the preparation of 4-methyl-4,5-dihydrotetrazolo [1,5-a] quinazolin-5-thione having the structural formula:

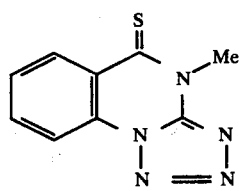

(Compound No. 46)

A mixture of 4-methyl-4,5-dihydrotetrazolo [1,5-a] quinazolin-5-one (2.0 g, prepared as described in Example 2), phosphorus pentasulphide (4.8 g) and acetonitrile (100 ml) was refluxed for 28 hours, cooled, diluted with water (150 ml) and 2N hydrochloric acid (40 ml) and extracted with chloroform. The extracts were washed with 1N sodium hydroxide solution and water, dried and evaporated. The residue (2.2 g) was recrystallised from ethanol to give the title compound (0.72 g, m.p. 192°–194°).

EXAMPLE 23

This example illustrates the preparation of 4-methyl-4,5-dihydrotetrazolo [1,5-a] quinazolin-5-thione by an alternative procedure to that described in Example 22.

A mixture of 4-methyl-4,5-dihydrotetrazolo [1,5-a] quinazolin-5-one (20 g, prepared as described in Example 2), phosphorus pentasulphide (46.5 g), dichloroethane (1.1) and bromine (6 ml) was stirred at room temperature for twenty minutes, then refluxed for four hours, with vigorous stirring. The hot mixture was filtered through kieselguhr the solid washed with hot chloroform and the total filtrate cooled and washed with N sodium hydroxide solution (2 × 500 ml) and brine. The solution was dried and evaporated and the residue triturated with carbon disulphide to give the title compound (19.78 g, m.p. 193°–5°). Recrystallisation from chloroform raised the m.p. to 196°–7°.

EXAMPLE 24

This example illustrates the preparation of 4-methyl-4,5-dihydrotetrazolo [1,5-a] quinazolin-5-thione by an alternative procedure to those described in Examples 22 and 23.

A mixture of 4-methyl-4,5-dihydrotetrazolo [1,5-a] quinazolin-5-one (200 mg), phosphorus pentasulphide (465 mg), mercuric chloride (270 mg), acetonitrile (1 ml) and dichloroethane (4 ml) was stirred at room temperature for fifteen minutes, then refluxed for ninety minutes. It was filtered hot, the precipitate washed with hot chloroform and the total filtrates cooled, washed with N sodium hydroxide solution and brine, and dried.

Evaporation and trituration of the residue with carbon disulphide gave the title compound (160 mg, m.p. 193-6°).

EXAMPLE 25

This example illustrates the preparation of three further thiones having the structural formulae:

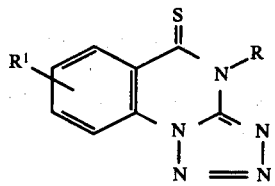

The corresponding tetrazolo [1,5-a] quinazolinones (prepared as described in either Examples 7 or 17) were treated with phosphorus pentasulphide/bromine, as described in Example 23, to give the thiones, shown in Table 4.

TABLE 4

| COMPOUND NO | $R^1$ | R | M.P. °C |
|---|---|---|---|
| 47 | H | $C_2H_5$ | 139 |
| 48 | 9-$CH_3$ | $CH_3$ | 175 |
| 49 | 7-Cl | $CH_3$ | 217 |

EXAMPLE 26

This example illustrates the preparation of a number of 5-imino-4-methyl-4,5-dihydrotetrazolo [1,5-a] quinazolines having the structural formulae:

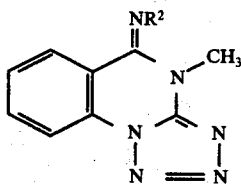

PROCEDURE A

A mixture of 4-methyl-4,5-dihydrotetrazolo [1,5-a] quinazolin-5-thione (4.4 g, prepared as described in Example 23), mercuric chloride (6.4 g), acetonitrile (150 ml) and an amine ($R^2NH_2$, excess) was refluxed, with stirring, for 1-2 hours. It was then filtered hot through kieselguhr, cooled and evaporated to give crude product (in the case of R = H, gaseous ammonia was introduced throughout the period of heating).

PROCEDURE B

The same quantities of reagents, but in N,N-dimethylformamide as solvent, were stirred at room temperature until reaction was complete (1-72 hours). The mixture was diluted with water and the crude product filtered off.

In both procedures the crude product was either recrystallised from a suitable solvent or preferably, where the product is not readily hydrolysed at room temperature, dissolved in dilute hydrochloric acid, filtered and reprecipitated with base.

TABLE 5

| COMPOUND NO | $R^2$ | M.P. °C | YIELD (%) | METHOD |
|---|---|---|---|---|
| 50 | H | 243 | 32 | A |

TABLE 5-continued

| COMPOUND NO | $R^2$ | M.P. °C | YIELD (%) | METHOD |
|---|---|---|---|---|
| 51 | $CH_3$ | 171 | 56 | A |
| 52 | $C_2H_5$ | 175 | 43 | B |
| 53 | n-$C_3H_7$ | 152 | 86 | B |
| 54 | iso-$C_3H_7$ | 156 | 48 | A |
| 55 | n-$C_4H_9$ | 149 | 43 | A |
| 56 | iso-$C_4H_9$ | 140 | 40 | A |
| 57 | n-$C_6H_{13}$ | 109 | 60 | B |
| 58 | n-$C_{10}H_{21}$ | ca. 170 | 27 | A |
| 59 | $CH_2C_6H_5$ | 158 | 54 | A |
| 60 | $C_6H_5$ | 177 | 43 | B |
| 61 | $CH_2CH_2OH$ | 160 | 29 | A |
| 62 | $NH_2$ | 186 | 64 | B |

EXAMPLE 27

This example illustrates the preparation, by an alternative procedure to that described in Example 26, of 5-imino-4-methyl-4,5-dihydrotetrazolo [1,5-a] quinazoline, having the structural formula:

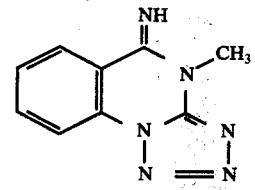

A mixture of 5-benzylimino-4-methyl-4,5-dihydrotetrazolo [1,5-a] quinazoline (2.46 g, prepared as described in Example 26), N-hydrochloric acid (125 ml) and 10% palladium on carbon (200 mg) was stirred under hydrogen for three hours, filtered and neutralised with base. The precipitate was dried and recrystallised from acetonitrile to give the title compound (0.43 g, m.p. 242-4°).

EXAMPLE 28

This example illustrates the preparation of the hydrochloride of 5-methylimino-4-methyl-4,5-dihydrotetrazolo [1,5-a] quinazoline having the structural formula:

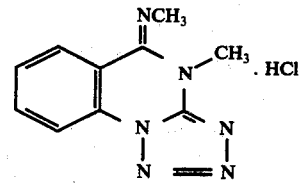

(Compound No. 63)

A solution of the base (1.0 g, prepared as described in Example 26) in chloroform was filtered and saturated with hydrogen chloride gas. The precipitate was filtered off and washed with chloroform and ether to give the title compound (1.07 g, m.p. 279°, decomp.).

EXAMPLE 29

This example illustrates an atomisable fluid comprising a mixture consisting of 25% by weight of Compound No. 2 of Example 2 and 75% by weight of xylene.

EXAMPLE 30

This example illustrates a dusting powder which may be applied directly to plants or other surfaces and comprises 1% by weight of Compound No. 2 of Example 2 and 99% by weight of talc.

EXAMPLE 31

25 Parts by weight of the product described in Example 2, 65 parts by weight of xylene, and 10 parts of an alkyl aryl polyether alcohol ('Triton' X-100; 'Triton' is a Trade Mark) were mixed in a suitable mixer. There was thus obtained an emulsion concentrate suitable for use in agriculture application.

EXAMPLE 32

5 Parts by weight of Compound No. 2 of Example 2 were thoroughly mixed in a suitable mixer with 95 parts by weight of talc. There was thus obtained a dusting powder.

EXAMPLE 33

This example illustrates a concentrated liquid formulation in the form of an emulsion. The ingredients listed below were mixed together in the stated proportions and the whole stirred until the constituents were dispersed.

|  | % wt. |
|---|---|
| Compound No. 2 (Example 2) | 20 |
| 'Lubrol' L ('Lubrol' is a Trade Mark) | 17 |
| Calcium dodecylbenzenesulphonate | 3 |
| Ethylene dichloride | 45 |
| 'Aromasol' H ('Aromasol' is a Trade Mark) | 15 |
|  | 100% |

EXAMPLE 34

The ingredients listed below were ground together in the proportions stated to produce a powdered mixture readily dispersible in liquid.

|  | % wt. |
|---|---|
| Compound No. 2 (Example 2) | 50 |
| 'Dispersol' T ('Dispersol' is a Trade Mark) | 5 |
| China Clay | 45 |
|  | 100% |

EXAMPLE 35

A composition in the form of grains readily dispersible in a liquid (for example water) was prepared by grinding together the first four of the ingredients listed below in the presence of water and then the sodium acetate was mixed in. The admixture was dried and passed through a British Standard mesh sieve, size 44–100 to obtain the desired size of grains.

|  | % Wt. |
|---|---|
| Compound No. 2 (Example 2) | 50 |
| 'Dispersol' T | 12.5 |
| Calcium lignosulphonate | 5 |
| Sodium dodecylbenzenesulphonate | 12.5 |
| Sodium acetate | 20 |
|  | 100% |

EXAMPLE 36

A composition suitable for use as a seed dressing was prepared by mixing all three of the ingredients set out below in the proportions stated.

|  | % Wt. |
|---|---|
| Compound No. 2 (Example 2) | 80 |
| Mineral Oil | 2 |
| China Clay | 18 |
|  | 100% |

EXAMPLE 37

A granular composition was prepared by dissolving the active ingredient in a solvent, spraying the solution obtained onto the granules of pumice and allowing the solvent to evaporate.

|  | % Wt. |
|---|---|
| Compound No. 2 (Example 2) | 5 |
| Pumice Granules | 95 |
|  | 100% |

EXAMPLE 38

An aqueous dispersion formulated was prepared by mixing and grinding the ingredients recited below in the proportions stated.

|  | % Wt. |
|---|---|
| Compound No. 2 (Example 2) | 40 |
| Calcium lignosulphonate | 10 |
| Water | 50 |
|  | 100% |

The following constitutes an explanation of the compositions or substances represented by the various Trade Marks and Trade Names referred to in the foregoing Examples.

| | |
|---|---|
| "LUBROL" L | is a condensate of 1 mole of nonyl phenol with 13 molar proportions of ethylene oxide. |
| "AROMASOL" H | is a solvent mixture of alkylbenzenes. |
| "DISPERSOL" T | is a mixture of sodium sulphate and a condensate of formaldehyde with the sodium salt of naphthalene sulphonic acid. |
| "LISSAPOL" NX | is a condensate of 1 mole of nonyl phenol with 8 moles of ethylene oxide. |
| "TRITON" X-100 | is an alkyl aryl polyether alcohol. |

EXAMPLE 39

Compositions containing compounds and compositions as defined herein were made up and tested against soil-borne fungal diseases. The two procedures used in these tests and the results obtained in each of them are shown hereinafter. The compounds tested, and the results obtained, are listed in the Table below.

TEST AGAINST PYTHIUM ULTIMIUM - PROCEDURE

Approximately one gram portions of culture of *Pythium ultimum* maintained on 2% malt agar test tube slopes at 20° C are transferred to about 400 grams of sterilised soil containing 5% maize meal in a 300 ml bottle. After 10 to 14 days the inoculated soil is mixed with sterile John Innes seed compost at a rate of 800 grams of soil culture to 32 litres of compost.

The mixture is moistened and covered and after three days is used as follows. Approximately 100 grams of the mixture is placed into a fibre pot and 10 pea seeds coated 2 days beforehand with chemical under test (a powdered dressing containing 25% by weight of the chemical was used) at the rate of 500 ppm are sprinkled on the surface of the soil. Another 100 grams of the mixed soil is then placed on top of the seeds and the pot is kept in the greenhouse at between 16° C and 22° C. A first count of emergent seedling is made after 10 days and another week is allowed to lapse before a second visual assessment takes place by pulling the seedlings up and inspecting their roots. Six replicates are conducted and observations are made of the number of healthy seedlings and the number of unhealthyl seedlings. The number of ungerminated seeds is less than the number of emergent seedlings. Controls wherein seed treated with thiram are used, are simultaneously carried out. Thiram is bis (dimethylthiocarbamoyl) disulphide. Calculations are then made whereby a grading is obtained for disease control.

TEST AGAINST FURARIUM CULMORUM -PROCEDURE

John Innes seedling compost is admixed with a culture of *Fusarium culmorum* grown on an admixture of soil and cornmeal and the entire mixture then wrapped in brown paper and incubated in the glasshouse for 48 hours. The incubated soil is placed in pots; then seeds (twenty per pot) treated with a 25% seed dressing formulation containing the chemical under test in concentration 1000 parts per million are sown in pots. Seeds treated with 'Agrosan' (Trade Mark) mercury seed dressing are used as a standard. Counts of the seedlings emergent 10 days after sowing are taken and the results converted to a percentage of the seeds sown. Disease assessments are made 16 days after sowing.

TEST AGAINST RHIZOCTONIA SOLANI - PROCEDURE

An inoculum of *Rhizoctonia solani* is added to a partially sterilised loam soil, to provide the latter with a 1% w/w content of the inoculum. The loam soil is then allowed to stand for one week so as to be completely colonised by the disease.

The test compound, as a 25% powder seed dressing formulation, is then admixed with the loam soil at a rate of 100 parts per million parts of soil (by weight). After standing for four days to allow the chemical to take effect plastic pots are half-filled with untreated partially sterilised, loam soil and cotton seeds sown on the surface thereof, whereafter the pots are topped up with the treated loam soil.

A control experiment is conducted with PCNB (pentachloronitrobenzene). The pots are then inspected and assessed 13 days later for disease.

The results of the three foregoing tests are set out in the Table below, expressed as gradings as follows:

| Grading | Significance of grading |
|---|---|
| 0 | No activity or up to 20% of the disease control given by standard |
| 1 | 20-75% of the disease control given by standard |
| 2 | 75-99% of the disease control given by standard |
| 3 | Degree of control equal to, or better than standard |

TABLE

| DISEASE | COMPOUND NO AND DISEASE GRADE |
|---|---|
| *Pythium ultimum* | 2(1), 6(1), 8(1), 24(2), 41(2), 42(1), 43(1), 46(3), 50(1), 52(1), 57(1) |
| *Fusarium culmorum* | 2(1), 3(2), 19(2). |
| *Rhizoctonia solani* | 3(2), 9(1), 10(1), 22(1), 58(1) |

In the above Table the test conducted with compounds nos. 6, 8, 41, 42, 43, 50, 52, 57 and 58 was a different procedure at a rate of 250 ppm as follows:

The test chemicals, were prepared in the same way as for the foliar sprays and soil drench experiments of Example 45. They were then applied at the rate of 250 parts per million (ppm) to John Innes compost which had been inoculated 24 hours previously with spores of the fungal disease being tested against. Pots of 1½ inches diameter containing the inoculated soil and lettuce or mustard seeds were placed in 10 millilitres of the solution of the test chemical. After 7 to 8 days seedling emergence was compared with that of a control pot placed in water alone. The results were graded on a scale 0 to 4 where 0 signifies no control of the disease and 4 signifies complete control.

EXAMPLE 40

Compound No. 2 (Example 2) was tested in two comparative experiments against the organism *Piricularia oryzae* (rice blast). For the purpose of these tests, which were root treatments of rice plants, the chemical was ground in a vibrating bead mill together with 2% by weight of 'Dispersol' T.

Sansanishiki rice seeds were sown in John Innes No. 1 Compost at the rate of 10 seeds per pot and allowed to germinate. At certain periods (see tables) thereafter the compost was soaked by standing the posts in liquid containing various rates of chemical and then inoculated with a suspension of spores in 0.05% 'Tween' 20 at a concentration of 200,000 spores per millilitre.

The inoculated seedlings were then incubated for 48 hours in a humidity cabinet at 75° F, and then transferred to a glasshouse at that temperature until assessment took place 5 days after inoculation.

The results of two replicates are expressed as disease gradings in the two Tables below for each experiment. Gradings of disease (visual assessment) level are:-

| Percentage of leaf area with lesions (disease) | Grading |
|---|---|
| 0 | 4 |
| 1-5 | 3 |
| 6-25 | 2 |
| 26-60 | 1 |
| 61-100 | 0 |

TABLE

| CHEMICAL COMPOUND | RATE OF APPLICATION (parts per million) | | | | |
|---|---|---|---|---|---|
| | 200 | 100 | 50 | 25 | 12.5 |
| 'Phosvel' | 0 | 0 | 0 | 0 | — |
| 'Kasumin' | 3 | 3 | 2 | 1 | — |
| Compound No. 2 | — | 4 | 3.5 | 2.5 | 1 |

TABLE

| Interval between treatment and inoculation in days | 2 | 4 | 7 | 11 |

TABLE-continued

| Age of plants at treatment in days | 12 | 10 | 7 | 3 |
|---|---|---|---|---|
| Rate of Application of compound (ppm a.i.) | | Grade of disease control | | |
| Compound No. 2    100 | 3, 3 | 3, 3 | 3, 3 | 3, 3 |
| 50 | 3, 2 | 3, 2 | 3, 2 | 3, 2 |
| 25 | 3, 3 | 1, 0 | 1, 1 | 2, 1 |
| 12.5 | 0, 0 | 0, 0 | 0, 0 | 1, 1 |
| 'Benlate'    100 | 3, 3 | 3, 3 | 3, 3 | 3, 3 |
| 50% a.i.    50 | 3, 3 | 3, 3 | 3, 3 | 3, 2 |
| 25 | 2, 2 | 1, 0 | 0, 1 | 0, 0 |
| 12.5 | 0, 0 | 0, 0 | 0, 0 | 0, 0 |

Control plants gave grade 0 throughout
(a.i. = active ingredient)

EXAMPLE 41

Compound No. 2 (Example 2) was tested against rice blast *(Piricularia oryzae)*. For the purpose of this test, which was a protectant spray test, the chemical was made up in 0.15% 'Tween 20'. 12-day old rice plants grown as described in Example 40 were sprayed with chemical and kept in a controlled environment. They were then inoculated with a suspension of spores in 0.05% 'Tween 20.' The infected seedlings were incubated, and then kept in the glasshouse for 5 days before assessment, as described in Example 40.

The results of two replicates are expressed as disease gradings in the Table below. The gradig scale is that set out in Example 40.

TABLE

| CHEMICAL | RATE OF CHEMICAL (ppm a.i.) | DISEASE GRADING |
|---|---|---|
| Control | | 0, 0 |
| | | 0, 0 |
| 'Rabcide' | 500 | 3, 2 |
| 98% a.i. | 200 | 2, 2 |
| | 100 | 0, 2 |
| 'Hinosan' | 200 | 3, 3 |
| 2% a.i. | 100 | 3, 3 |
| 'Kasumin' | 200 | 3, 3 |
| 50% a.i. | 100 | 3, 2 |
| 'Panoctine' | 500 | 2, 1 |
| 100% a.i. | 200 | 2, 2 |
| | 100 | 3, 2 |
| No. 2 of | 500 | 3, 3 |
| Example 2 | | |
| | 200 | 3, 3 |
| | 100 | 2, 3 |

EXAMPLE 42

Compound No. 2 (Example 2) was tested against rice blast (*Piricularia oryzae*). For the purpose of this test which was as a seed treatment the chemical was made up in form of a very finely divided dispersion of a solid chemical with Dyapol PT in water.

Sasanishiki rice seed was treated with the formulated chemical in a high speed rotary mixer for ½ minute, and then transferred to a ball mill for 1 hour to uniformly coat the seeds. The seeds were sown in John Innes No. 1 compost, allowed to germinate and inoculated with a spore suspension in 0.15% 'Tween 20' at various intervals.

Assessment was similar to Examples 40 and 41 and carried out 5 days after each inoculation.

The results of two replicates are expressed as disease gradings in the Table below. The grading scale is that set out in Example 40.

TABLE

| CHEMICAL | RATE OF APPLICATION OF CHEMICAL (ppm a.i.) | AGE OF PLANT IN DAYS AT INOCULATION | | | | | |
|---|---|---|---|---|---|---|---|
| | | 16 | 21 | 28 | 35 | 42 | 49 |
| Control | | 0, 1 | 0, 0 | 0, 0 | 1, 0 | 0, 0 | 0, 0 |
| Compound No. 2 (Ex. 2) | 16000 | 4, 4 | 4, 4 | 4, 4 | 4, 4 | 3, 4 | 4, 3 |
| " | 8000 | 4, 4 | 3, 3 | 3, 2 | 3, 2 | 3, 2 | 3, 3 |
| " | 4000 | 3, 3 | 3, 2 | 2, 3 | 3, 3 | 3, 1 | 3, 3 |
| " | 2000 | 3, 3 | 2, 2 | 3, 2 | 2, 3 | 1, 2 | 2, 2 |
| " | 1000 | 0, 2 | 1, 2 | 2, 2 | 3, 3 | 2, 2 | 3, 2 |

EXAMPLE 43

Compound No. 2 (Example 2)was tested against *Piricularia oryzae* (rice blast). For the purpose of this test, designed to determine persistence as a root treatment, the compound was made up as described in Example 40.

Ten day old rice seedlings were grown and treated with chemical as described in Example 40. They were then inoculated with a suspension of spores in the same way 4, 11 and 18 days after treatment. Assessment was conducted in the same way as described in Example 40, 5 days after inoculation.

The results of two replicates are expressed as Disease gradings in the Table below. The grading scale is that set out in Example 40.

TABLE

| CHEMICAL TREATMENT | RATE OF APPLICATION OF CHEMICAL (ppm a.i.) | INTERVAL IN DAYS BETWEEN TREATMENT AND INOCULATION | | |
|---|---|---|---|---|
| | | 4 | 11 | 18 |
| Untreated (Control) | | 0, 0 | 0, 0 | 0, 0 |
| 'Kasumin' | 1000 | 3, 2 | 0, 0 | 0, 0 |
| 50% a.i. | 500 | 2, 2 | 0, 0 | 0, 0 |
| | 250 | 3, 3 | 0, 0 | |
| | 125 | 3, 2 | 0, 0 | |
| | 62.5 | 1, 2 | 0, 0 | |
| Compound No. 2 of Example 2 | 1000 | 3, 3 | 3, 3 | 3, 3 |
| | 500 | 3, 3 | 3, 3 | 3, 3 |
| | 250 | 2, 1 | 3, 3 | 3, 3 |
| | 125 | 3, 2 | 3, 2 | 2, 2 |
| | 62.5 | 0, 2 | 1, 0 | |

EXAMPLE 44

This example illustrates the efficacy of Compound No. 2 against rice blast (*Piricularia oryzae*) as a root treatment on large rice plants.

Nine week old Sasanishiki rice plants were washed at the roots and allowed to stand in liquid preparations of the test chemical for either 10 minutes or overnight. The plants were then placed in pots of John Innes No. 1 Compost, inoculated after 4 days, and assessed after a further 7 days.

The results of two replicates are expressed as disease gradings in the Table below. The grading scale is that set out in Example 40.

TABLE

| CHEMICAL TREATMENT | RATE OF APPLICATION OF CHEMICAL (ppm a.i.) | TREATMENT TIME | |
|---|---|---|---|
| | | 10 MINUTES | OVERNIGHT |
| Control (Untreated) | | 1, 0 | 1, 0 |
| 'Kasumin' | 2000 | 2, 1 | — |
| 50% a.i. | 1000 | 2, 1 | 1, 1 |
| | 500 | — | 1, 1 |
| Compund | 2000 | 2, 3 | — |

TABLE-continued

| CHEMICAL TREATMENT | RATE OF APPLICATION OF CHEMICAL (ppm a.i.) | TREATMENT TIME | |
|---|---|---|---|
| | | 10 MINUTES | OVERNIGHT |
| No. 2 of Example 2 | 1000 | 3, 3 | 3, 3 |
| | 500 | — | 3, 3 |

"—" means not tested.

EXAMPLE 45

The compounds prepared according to Examples 1 to 28 (that is Compounds Nos 1 to 63) were tested against a variety of foliar fungal diseases of plants. The technique employed is to spray the foliage of the undiseased plants with a solution of the test compound and also to drench the soil in which the plants are growing with another solution of the test compound.

All solutions for spraying contained either 100 or 200 ppm (parts per million) of the test compound. All the soil drench solutions also, correspondingly, contained either 100 or 200 ppm of the test compound.

The plants were then infected with the disease it was desired to control and after a period of days, depending upon the particular disease, the extent of the disease was visually assessed. The results are given below, in the form of a grading as follows:-

| Grading | Percentage Amount of Disease |
|---|---|
| 0 | 61 to 100 |
| 1 | 26 to 60 |
| 2 | 6 to 25 |
| 3 | 0 to 5 |
| 4 | 0 |

In the first Table below, the disease is given in the first column, whilst in the second column is given the time which elapsed between infecting the plants and assessing the amount of disease. The third column assigns to each disease a code letter, these code letters being used in the later Tables to identify the diseases. The rate of application used in the second Table was 100 ppm and in the third Table it was 200 ppm.

TABLE

| DISEASE AND PLANT | TIME INTERVAL (DAYS) | DISEASE CODE LETTER |
|---|---|---|
| Phytophthora infestans (tomato) | 3 | A |
| Plasmopara viticola (vine) | 7 | B |
| Piricularia oryzae (rice) | 7 | C |
| Podosphaera leucotricha (apple) | 10 | D |
| Botrytis cinerea (broad bean) | 3 | E |
| Erysiphe graminis (wheat or barley) | 7 | F |

100 PPM RATE

| COMPOUND NO. | DISEASE CODE LETTER AND GRADING | | | | | |
|---|---|---|---|---|---|---|
| | A | B | C | D | E | F |
| 1 | 1 | 0 | 0 | 0 | 1 | 2 |
| 2 | — | 0 | 3 | — | 0 | — |
| 3 | — | 0 | 2 | — | 2 | — |
| 9 | 1 | — | 3 | 3 | 0 | — |
| 10 | 2 | — | 0 | 3 | 0 | — |
| 11 | 0 | 0 | 0 | 1 | 0 | — |
| 12 | 0 | 0 | 0 | 1 | 3 | — |
| 15 | 0 | 1 | 1 | 3 | 0 | — |
| 16 | 2 | 0 | 1 | 1 | 0 | — |
| 18 | 1 | 0 | 1 | 3 | 0 | — |
| 20 | 0 | 3 | 0 | 3 | 0 | — |
| 21 | 0 | 2 | 0 | 0 | 0 | — |
| 22 | 1 | 0 | 0 | 2 | 0 | — |
| 23 | 1 | 0 | 0 | 1 | 0 | — |
| 24 | 2 | 0 | 2 | 0 | 3 | 0 |
| 27 | 0 | 0 | 0 | 0 | 0 | 0 |
| 32 | 0 | 0 | 0 | 4 | 0 | 0 |
| 33 | 2 | 4 | 0 | 0 | 3 | — |
| 34 | 1 | 0 | 1 | 1 | 0 | 0 |
| 36 | 1 | 0 | 0 | 0 | 1 | — |
| 37 | 0 | 0 | 3 | 0 | 1 | — |
| 38 | 0 | 0 | 2 | 1 | 0 | 3 |
| 46 | 0 | 0 | 4 | 0 | 0 | 0 |

200 PPM RATE

| COMPOUND NO. | DISEASE CODE LETTER AND GRADING | | | | | |
|---|---|---|---|---|---|---|
| | A | B | C | D | E | F |
| 25 | 4 | — | 2 | — | 1 | 0 |
| 28 | 0 | 0 | 0 | 0 | 0 | 0 |
| 29 | 0 | 0 | 2 | 0 | 0 | 4 |
| 30 | 0 | 0 | 2 | 0 | 0 | 0 |
| 35 | 1 | 0 | 2 | 0 | 0 | 4 |
| 39 | 0 | — | 3 | — | 1 | 3 |
| 40 | 2 | 0 | 3 | — | 1 | 0 |
| 42 | 1 | 0 | 1 | — | 0 | 0 |
| 43 | 0 | 0 | 0 | — | 0 | 1 |
| 44 | 0 | — | 1 | — | 0 | 0 |
| 46 | 0 | 0 | 4 | 0 | 0 | 0 |
| 47 | 0 | — | — | — | 0 | 1 |
| 48 | 0 | — | 0 | — | 0 | 1 |
| 50 | 0 | — | 3 | — | 3 | 2 |
| 51 | 4 | — | 4 | — | 0 | 0 |
| 52 | 0 | — | 3 | — | 1 | 1 |
| 53 | 0 | — | 0 | — | 2 | 0 |
| 54 | 0 | — | 3 | — | 2 | 0 |
| 55 | 3 | — | 3 | — | 2 | 0 |
| 56 | 0 | — | 0 | — | 0 | 1 |
| 57 | 0 | — | 0 | — | 2 | 1 |
| 58 | 1 | — | 0 | — | 0 | 0 |
| 59 | 4 | — | 2 | — | 2 | 0 |
| 60 | 0 | — | 1 | — | 0 | 0 |
| 61 | 4 | — | 4 | — | 0 | 2 |
| 62 | 0 | — | 2 | — | 1 | 1 |
| 63 | 4 | — | 4 | — | 0 | 2 |
| 65 | 0 | 0 | 0 | — | 0 | 1 |
| 66 | 0 | 0 | 0 | — | 3 | 0 |
| 67 | 0 | 2 | 0 | — | 0 | 0 |
| 68 | 1 | 0 | 0 | — | 0 | 0 |

EXAMPLE 46

Derivatives according to the invention were tested against general foliage-borne bacterial plant diseases in the glasshouse. The anti-bacterial screening method employs high humidity to aid infection of treated plants. The derivatives proved to have some activity as an antibacterial spray under these conditions.

Different experimental formulations were tested. The tests were carried out on fireblight of pears, rice blight and tomato spot.

Pear, tomato and rice seedlings were sprayed and/or root drenched with an aqueous solution containing 100 or 200 ppm of the test chemical. After 48 hours they were inoculated with the appropriate disease organism; *Erwinia amylovora* (fire blight) on pears, *Xanthomonas vesicatoria* (bacterial leaf spot) of peppers and *Xanthomonas oryzae* (rice blight) on rice. Inoculations were accompanied by wounding the plants which is necessary for bacterial infection to take place. Immediately afterwards the plants were placed under a mist propagator or in a humidity cabinet. Symptoms were assessed on a 0–4 scale as shown below after up to 8 days. Results are shown in the Table which then follows.

| Grade | Percentage Amount of disease |
|---|---|
| 0 | 61–100% |
| 1 | 26–60% |
| 2 | 6–25% |
| 3 | Up to 5% |
| 4 | Disease free plants |

EXAMPLE 47

The activity of the active derivatives against a wide variety of plant bacterial and fungal diseases was investigated by in vitro tests as follows. The compounds were incorporated into 2% malt agar, from an aqueous dispersion or a solution in organic solvent, at a rate calculated to give a final concentration of 200 ppm active material. Two ml of a streptomycin preparation containing 100 units per milliliter was added to the malt agar to prevent bacterial contamination of the fungal tests.

The agar preparations were dried overnight in petri dishes and inoculated the following morning with the bacterial or fungal diseases using a multipoint inoculator. The antibacterial activity was assessed after 5 days and the antifungal activity after 6 days.

The results of the tests are set out below in the Table.

| DISEASE NAME (in Latin) | CODE LETTER FOR DISEASE | DISEASE TYPE |
|---|---|---|
| Cladosporium sphaerospermum | a | F |
| Pullularia pullalans | b | F |
| Alternaria tenuis | c | F |
| Chaetomum globosum | d | F |
| Aspergillus niger | e | F |
| Trichoderma viride | f | F |
| Algae (scenedesmus) | g | A |
| Penicillium digitatum | h | F |
| Gloeosporium musarum | i | F |
| Botrytis cinerea | j | F |
| Fusarium culmorum | k | F |
| Geotrichum candidum | l | F |
| Erwinia carotovora | m | B |
| Pseudomonas tomato | n | B |
| Xanthomonas malvacearum | o | B |
| Pseudomonas syringae | p | B |

* B signifies a Bacterial disease.
F signifies a Fungal disease.
A signifies an Alga.

TABLE

| COMPOUND NO | a | b | c | d | e | f | g | h | i | j | k | l | m | n | o | p |
|---|---|---|---|---|---|---|---|---|---|---|---|---|---|---|---|---|
| 33 | A | A | A | A | A | A | I | A | A | A | A | A | A | A | A | A |
| 24 | A | A | — | — | A | I | I | A | I | A | A | I | I | I | A | I |

"A" signifies activity against the disease.
"I" signifies no activity against the disease.
"—" signifies no test carried out.

EXAMPLE 48

This Example illustrates the activity of the com-

TABLE

DISEASE AND CONTROL GRADING (RATE OF APPLICATION 100 PPM)

| COMPOUND NO | X. oryzae PROTECTANT TEST | X. oryzae ROOT DRENCH TEST | X. vesicatoria PROTECTANT TEST | X. vesicatoria ROOT DRENCH TEST | E. amylovora PROTECTANT TEST | E. amylovora ROOT DRENCH TEST |
|---|---|---|---|---|---|---|
| 12 | 2–3 | 0 | 2 | 0 | 0–3 | 2–3 |
| 19 | 0 | 0 | 0 | 0 | 0–2 | — |
| 24 | 0 | 0 | 2–3 | 0–1 | — | — |
| 33 | 2–3 | 0 | 2 | 0 | — | — |
| 38 | 4 | 1–2 | 4 | 1–2 | — | — |
| 51 | 3 | 0 | 0 | 1 | — | — |
| 59 | 3 | 0 | 2–3 | 0 | — | — |
| 63 | 0–3 | 1 | 0–2 | 2 | — | — |

In a combined test in which the plants were both protectant sprayed and root drenched with test chemical at a rate of 200 ppm Compound No. 19 scored a grading of 4 against the disease *Erwinia amylovora*.

pounds and compositions of the invention against a number of fungal pathogens in an in vitro procedure as follows.

A plug of inoculum of 7 mm diameter, cut from an actively growing colony of the fungus, was placed on an agar plate containing the chemical and then incubated for up to 7 days. The amount of mycelial growth was then compared with that on nutrient agar in the absence of the chemical.

The first Table below sets out the fungal pathogens featured in the test, and ascribes to them a code letter. There then follows a key to the grading codes in which the results are expressed in the second Table following on therefrom.

TABLE OF DISEASES

| DISEASE NAME (in Latin) | DISEASE CODE LETTER |
|---|---|
| Pythium ultimum | a |
| Fusarium culmorum | b |
| Rhizoctonia solani | c |
| Alternaria tenuis | d |
| Septoria nodorum | e |
| Colletotrichum coffeanum | f |
| Piricularia oryzae | g |
| Fusarium oxysporum | h |
| Cochliobolus miyabeanus | i |
| Phytophthora cinnamomi | j |

DISEASE GRADING CODE
0 signifies complete growth of disease.
1 signifies slight growth stunting.
2 signifies very little growth.
3 signifies no growth.

TABLE OF RESULTS

| COMPOUND NO | DISEASE CODE LETTERS AND GRADINGS | | | | | | | | |
|---|---|---|---|---|---|---|---|---|---|
|  | a | b | c | d | e | f | g | h | i | j |
| 39 | 0 | 1 | 2 | 2 | 2 | 3 | 3 | 1 | 2 | 2 |
| 46 | 0 | 0 | 1 | 1 | 2 | 1 | 1 | 1 | 1 | 2 |
| 52 | 0 | 0 | 1 | 1 | 1 | 1 | 1 | 1 | 2 | 2 |
| Untreated control | 0 | 0 | 0 | 0 | 0 | 0 | 0 | 0 | 0 | 0 |

EXAMPLE 49

This example illustrates the in vivo use of the active compounds and compositions of the invention, to combat post-harvest fungal infections affecting oranges. Various compositions containing the active compounds were used, and compared with the compound known by the British Standards Institution common name benomyl (1-n-butyl carbamoyl-2-benzimidazole carbamic acid methyl ester). The test conducted was an eradicant and protectant dip-test against the disease *Penicillium digitatum* (green mould of citrus). The procedure adopted was as follows:

Four discs 10 mm in diameter, of orange peel, are dipped in aqueous suspensions containing 50 parts per million (ppm) of test chemical either (in eradicant tests) 1 day after incoulation with either *Penicillium digitatum* spore suspension $10^6$ cells/ml) or (in protectant tests) 3 hours before. The discs are randomly placed in replicates plastic "Replidishes" in which the relative humidity is kept high with moist filter paper for 1 week. The discs are scored for disease on a 0–4 scale. If all discs were completely healthy the treatment scored a 4; if only three dishes were healthy it scored a 3; if only two discs were healthy it scored a 2; if only one a 1, or if none were healthy the score was 0. Both eradicant and protectant treatments were assessed together. The results are set out in the Table below.

"Replidish" is a Trade Mark for a 10 × 10 centimeter petri dish sub-divided into 25 cube compartments sealed off from each other by a vertical plastic partition.

TABLE

| COMPOUND NO | DISEASE GRADING (RATE OF APPLICATION - 50 PPM) |
|---|---|
| 2 | 2–3 (Protectant Test) |
| 24 | 3 (Eradicant Test) |

EXAMPLE 50

This Example illustrates the activity of some of the invention compounds and procedure was as follows.

A suspension of *Scenedesmum spp* is added to a solution/suspension/or emulsion of the compound to give a final concentration of 5 ppm. After up to 5 days in a constant environment room the amount of algal growth is assessed by comparing the colour of the chemical, and grading is accorded on a 0–4 arbitrary scale where 0 is no control of the growth and 4 is complete kill of algal growth.

TABLE

| COMPOUND NO | RATE OF APPLICATION (ppm) | GRADING SCORE |
|---|---|---|
| 5 | 5 | 4 |
| 13 | 5 | 2 |
| 14 | 5 | 1 |
| 15 | 5 | 4 |
| 26 | 5 | 4 |
| 31 | 5 | 2 |
| 40 | 5 | 3 |
| 41 | 5 | 4 |
| 42 | 5 | 4 |
| 44 | 5 | 1 |
| 45 | 5 | 3 |
| 51 | 5 | 3 |
| 53 | 5 | 4 |
| 54 | 5 | 4 |
| 56 | 5 | 1 |
| 58 | 5 | 3 |

EXAMPLE 51

This Example illustrates the activity of Compound No. 2 against the disease *Colletotrichum lindemuthianum* on beans. The procedure conducted was as follows.

The test compound was applied to the leaves of dwarf French bean seedlings, var 'Prince' and/or to the soil. After 2 days the leaves were inoculated with a suspension of *Colletotrichum lindemuthianum* spores, placed in a humidity cabinet for 24 hours and the disease control obtained compared with untreated control plants after 5–6 days. The lesions appearing on the veins were graded and are given in the Table below. The key to the code follows afterwards.

TABLE

| COMPOUND NO | DISEASE GRADE (3 REPLICATES) | |
|---|---|---|
|  | FOLIAGE SPRAY AT 50 PPM RATE | ROOT DRENCH AT 50 PPM RATE |
| 2 | 2-3-2 | 2-3-2 |
| Untreated Control | 0-0-0 | 0-0-0 |

The foilage spray was applied 1 day before inoculation and the root drench 2 days before inoculation.

The grading code key for the above Table is set out below.

| Grade | Percentage Amount of Disease |
|---|---|
| 0 | 61–100% |
| 1 | 26–60% |
| 2 | 6–25% |
| 3 | Up to 5% |
| 4 | Disease free plants |

EXAMPLE 52

This Example further illustrates the activity of Compound No. 2 of this invention against the disease *Piricularia oryzae* (rice blast).

In this particular test the rice plants were 'upland' grown, that is grown in fields as opposed to paddy rice.

Rice seed treated in the manner set out in Example 42 was planted in fields in the Philippines in 1974 and eight weeks after sowing levels of infection with the disease were recorded. The means disease grade of 3 replicate plots (see key below) recorded was 2.3, against a grade of 3.3 for rice plants in a control experiment grown from untreated seed.

| GRADING | PERCENTAGE AMOUNT OF DISEASE PRESENT |
|---|---|
| 1 | less than 10% |
| 2 | between 11 to 25% |
| 3 | between 26 to 35% |
| 4 | between 36 to 50% |
| 5 | more than 50% |

The rate of application of the chemical to the seed was 4,000 ppm (parts per million).

We claim:

1. A process for combating the disease Piricularia oryzae, rice blast, which comprises applying to rice seeds, rice plants, the roots of rice plants, or to their locus within or remote from a germination or growing environment, an effective amount of a dihydrotetrazolo[1,5-a]quinazoline having the structural formula:

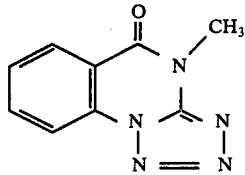

and chemical name: 4 methyl-4,5-dihydro tetrazol[1,5-a]quinazolin-5-one.

2. A process for combating the disease Piricularia oryzae, rice blast, which comprises applying to rice seeds, rice plants, the roots of rice plants, or to their locus within or remote from a germination or growing environment, an effective amount of a dihydrotetrazolo[1,5-a]quinazoline having the structural formula:

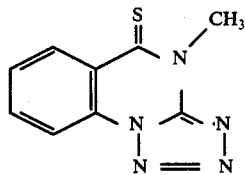

and chemical name: 4-methyl-4,5-dihydrotetrazolo [1,5-a]quinazolin-5-thione.

* * * * *